United States Patent
Kosik et al.

(10) Patent No.: US 8,115,657 B2
(45) Date of Patent: Feb. 14, 2012

(54) REMOTE DEVICE FOR CONTROLLING A COMPUTER BY A PHYSICALLY LIMITED PERSON

(75) Inventors: Leonid Andreevich Kosik, Moscow (RU); Aleksey Leonidovich Kosik, Moscow (RU); Taras Leonidovich Kosik, Moscow (RU)

(73) Assignee: Gravitonus Inc., Fairfax, VA (US)

( * ) Notice: Subject to any disclaimer, the term of this patent is extended or adjusted under 35 U.S.C. 154(b) by 640 days.

(21) Appl. No.: 12/304,128

(22) PCT Filed: Jan. 29, 2007

(86) PCT No.: PCT/RU2007/000042
§ 371 (c)(1),
(2), (4) Date: Dec. 10, 2008

(87) PCT Pub. No.: WO2008/004905
PCT Pub. Date: Jan. 10, 2008

(65) Prior Publication Data
US 2009/0278712 A1    Nov. 12, 2009

(30) Foreign Application Priority Data
Jul. 7, 2006 (RU) .................................. 2006124413

(51) Int. Cl.
*H03M 11/00* (2006.01)
(52) U.S. Cl. ............ 341/21; 345/157; 345/156; 341/20; 600/534; 600/590; 710/73
(58) Field of Classification Search ............ 341/20, 341/21; 345/156, 157; 710/73; 600/534, 600/590
See application file for complete search history.

(56) References Cited

U.S. PATENT DOCUMENTS 5,233,662 A     8/1993   Christensen
5,460,186 A *  10/1995   Buchhold ............... 600/590
5,523,745 A *   6/1996   Fortune et al. ............ 340/4.12
(Continued)

FOREIGN PATENT DOCUMENTS

| DE | 4100402 A1 | 7/1991 |
| RU | 2245692 | 2/2005 |
| RU | 2269325 | 2/2006 |

*Primary Examiner* — Albert Wong
(74) *Attorney, Agent, or Firm* — Defillo & Associates, Inc.; Evelyn A. Defillo

(57) ABSTRACT

The invention relates to medicine and can be used for persons with paralysis of upper and lower limbs. The inventive device comprises a signal processing and transmitting module (1), a coordinate unit (2), functional contacts (3), control contacts (4) and an elastic base plate (5) which is symmetrical with respect to a longitudinal axis and is provided with an unbendable projection (6) on the front part thereof. The plate consists of a central circle (7), peripheral circles (8) which are radially spaced away from the central circle, connecting straps (9) mating with the central circle (7) by one end thereof, whilst the other end is coupled with the respective peripheral circle (8). The unbendable projection is made in a shape of an equilateral trapezoid adjacent to the central circle by the larger base thereof and is upwardly bent at about 20 to 60° angle with respect to the plate plane. The signal processing and transmitting module is arranged on the top surface of the central circle of the plate. The coordinate unit is arranged on the lower surface of the central circle. Each functional contact is fixed to the lower surface of the respective peripheral circle. The control contacts are fixed to the lower surface of the unbendable projection. The plate together with operating elements fixed thereto is enveloped with a waterproof film (10). The shape of the film matches the external outlines of the plate with edge allowance (11) and the edge thereof is provided with V-shaped notches (12). Said invention makes it possible to improve the operational characteristics, to simplify the production of the device and to reduce the costs thereof.

1 Claim, 3 Drawing Sheets

U.S. PATENT DOCUMENTS

| | | | | |
|---|---|---|---|---|
| 5,603,065 A | * | 2/1997 | Baneth | 710/73 |
| 6,222,524 B1 | * | 4/2001 | Salem et al. | 345/157 |
| 6,400,353 B1 | * | 6/2002 | Ikehara et al. | 345/157 |
| 7,071,844 B1 | * | 7/2006 | Moise | 341/21 |
| 7,580,028 B2 | * | 8/2009 | Jeong et al. | 345/156 |
| 7,768,499 B2 | * | 8/2010 | Sturtz | 345/157 |

\* cited by examiner

US 8,115,657 B2

REMOTE DEVICE FOR CONTROLLING A COMPUTER BY A PHYSICALLY LIMITED PERSON

CROSS REFERENCE TO RELATED APPLICATION

This application is a national stage entry of PCT/RU2007/000042 filed Jan. 29, 2007, under the International Convention claiming priority over Russian application No. RU 2006124413 filed Jul. 7, 2007.

TECHNICAL FIELD

The invention relates to medicine and can be used for persons with paralysis of upper and lower limbs, with absent limbs, as well as an additional loop computer control for persons whose occupation limits the use of hands.

BACKGROUND OF THE INVENTION

Persons with quadriplegia (total paralysis of both the upper and lower limbs) cannot do anything with their hands. At strong affection of the spinal cord the conscious control of skeletal muscles is completely broken. Only the groups of maxillofacial and tongue muscles are functional as they are innervated by cranial nerves. Besides, the use of hands is sometimes difficult or impossible, or insufficient (for example, at simultaneous input of several commands) while working on a computer.

There is known a remote device for controlling a computer by physically limited person including at least one make and break contact, a device specifying coordinates that determine functioning of peripherals, and a signal-processing unit energizing the signal receiving part of the unit, electronic part and transmitter-receiver (WO 03/013402 A1, 20.02.2003).

This device allows to remotely control computer by affecting the joystick by the tongue muscles, however, the structure does not consider the individual peculiarities of the patient oral cavity and specifics of the tongue control; the electronic part of the unit is located outside the oral cavity as the outer structure is held by teeth, at that the maxillofacial muscles are constantly tense and the front teeth cannot be used in operation. Besides, the device is pretty complicated for manufacturing due to numerous operating elements connected with each other kinematically.

There is also known a remote device for controlling a computer by physically limited person according to RU Patent No. 2245692 C2 (10.02.2005).

This device, though provides effective control of peripherals (computer) with the help of the maxillofacial muscles, tongue muscles and teeth of a person, is more convenient for use and more manufacturable than the one known from WO 03/013402, as totally located in the oral cavity, however, it is manufactured strictly in accordance with the individual peculiarities of an oral cavity of a specific person.

There is also known a remote device for controlling a computer by physically limiter person (prototype) made to allow its location in the oral cavity and including, like the announced, a signal processing and transmitting module, a coordinate unit electrically connected with the module that controls the cursor, at least three functional contacts for the computer keyboard functions remote control and at least two control contacts electrically connected with the module performing mouse buttons functions (RU 2269325 C1, 10.02.2006).

In the device of Patent RU 2269325, the electronic signal processing and transmitting module, coordinate unit, functional contacts for the computer keyboard functions remote control, control contacts that perform mouse buttons functions and connecting wires are located in the single case that, in its turn, is fixed on a basis made in accordance with the impression of a jaw of a specific user. Therefore, different devices shall be made for different users, which will correspond to their anthropometric parameters. Such piecework production significantly limits the range of users and makes the device expensive and too complicated for manufacturing and use thereof. Besides, the basis and the device case located on it prevent the tongue contact with sensitive receptors of the hard palate mucosa, which impedes orientation of the latter in the oral cavity and makes it impossible to position it (tongue) accurately on the device controls, which, in its turn, leads to false commands. All the above mentioned deteriorates the operating characteristics and complicates technology for mass production of such device.

SUMMARY OF THE INVENTION

The object of the present invention is to provide a non-personified remote device for controlling a computer by physically limiter persons that is able to accommodate (adapt) to the oral cavity of any anthropometric size and form and therefore can be used by any person. Besides, the device shall not prevent the control of the tongue movement inside the oral cavity, the tongue contact with the receptors of the hard palate mucosa and accurate positioning of it on the controls. Additionally, the device shall be fixed in the oral cavity and pulled out from it without hands assistance and outside assistance. Finally, the device shall be fabricable for machine production that makes it inexpensive and available for wide application.

Thus, the technical result, which is achieved when the invention is carried out is improvement of operating characteristics, as well as simplification and reduction of the cost of the device fabrication method.

Said technical result can be achieved by the fact that the remote device for controlling a computer by physically limiter person made to allow its location in the oral cavity and including the signal processing and transmitting module, the coordinate unit electrically connected with the module and controlling the cursor, at least three functional contacts for the computer keyboard functions remote control and at least two control contacts electrically connected with the module performing the mouse buttons functions, the device comprising the basic plate which is symmetrical with respect to longitudinal axis and is provided with the unbendable projection on the its front part. The plate consists of the central circle, at least three peripheral circles which are radially spaced away from the central circle, at least three connecting straps mating with the central circle by one end thereof, whilst the other end is coupled with the respective peripheral circle. The unbendable projection is made in the shape of equal trapezium adjacent to the central circle by the lager base thereof and is upwardly bent at about 20 to 60° angle with respect to the plate plane. The signal processing and transmitting module is arranged on the top surface of the central circle of the plate. The coordinate unit is arranged on the lower surface of the central circle of the plate. Each functional contact is fixed on the lower surface of the respective peripheral circle of the plate. The control contacts are fixed on the lower surface of the unbendable projection. The plate together with operating elements fixed thereto is enveloped with the waterproof film, which shape matches the external outlines of the plate with edge allowance and the edge thereof is provided with a plurality of V-shaped notches.

DESCRIPTION OF THE PREFERRED EMBODIMENT

Figure 1:
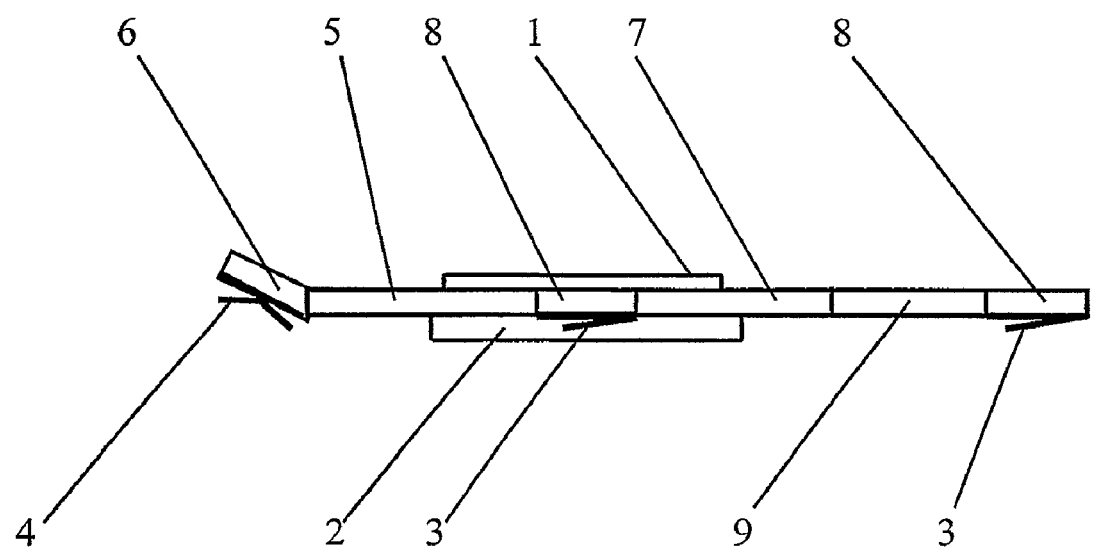
FIG. 1 shows a general view of the remote device for controlling the computer (the side view without the cover film).
Figure 2:
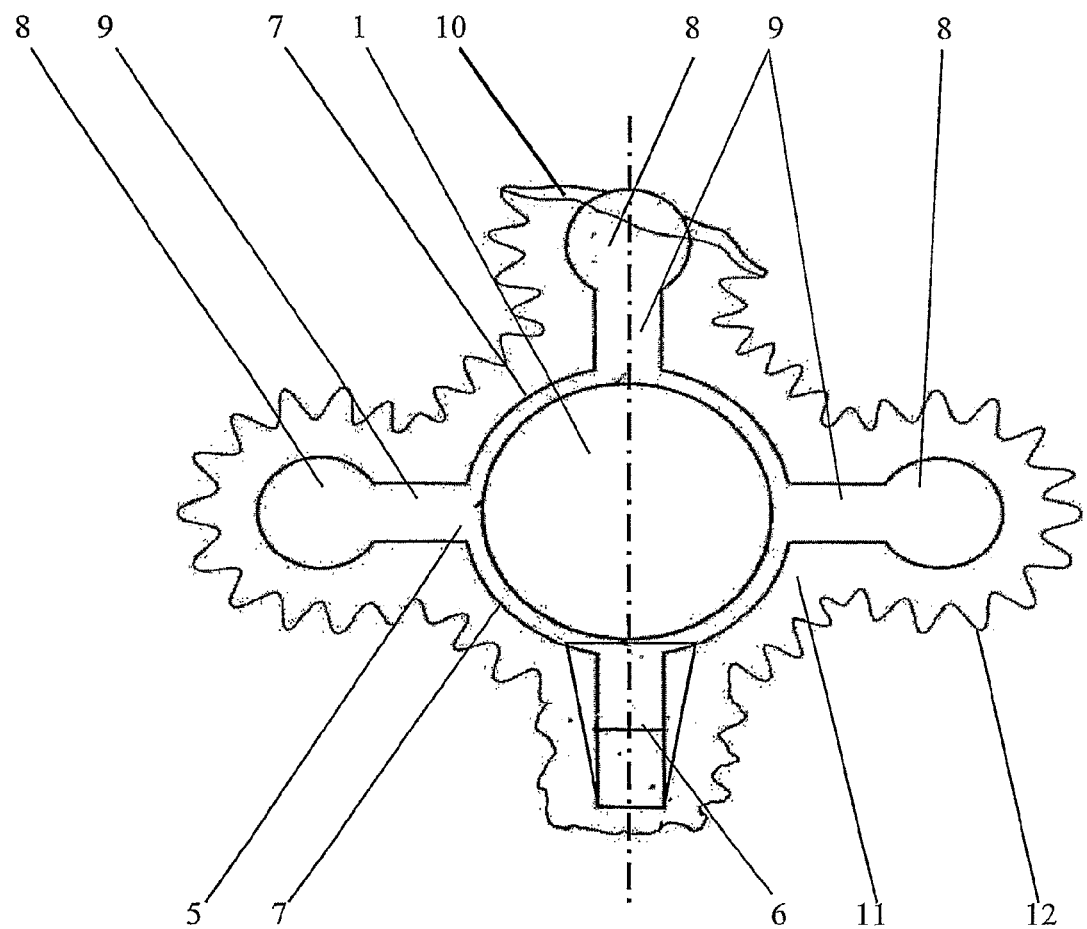
FIG. 2 shows a plan view of the remote device for controlling the computer.

The remote device for controlling the computer by the physically limited person includes the signal processing and transmitting module (1), the coordinate unit (2) specifying coordinates and operating the cursor of the computer, at least three functional contacts (3) electrically connected with the module (1) for the remote control of the computer keyboard functions, at least two control contacts (4) electrically connected with the module (1) and performing the mouse buttons functions. The device comprises the elastic basic plate (5) which is symmetrical with respect to the longitudinal axis and is providing with the unbendable projection (6) on the front part thereof. The plate (5) consists of the central circle (7), at least three peripheral circles (8) which are radially spaced away from the central circle (7), at least three connecting straps (9) (according to the number of the functional contacts) mating with the central circle (7) by one end thereof, whilst the other end is coupled with the respective peripheral circle (8). The unbendable projection (6) is made in the shape of equal trapezium adjacent to the central circle (7) by the larger base thereof and is upwardly bent at the about 20 to 60° angle with respect to the plate plane. The signal processing and transmitting module (1) is arranged on the top surface of the central circle (7) of the plate (5). The coordinate unit (2) is located on the lower surface of the central circle (7) of the plate (5). Each functional contact (3) is fixed on the lower surface of the respective peripheral circle (8) of the plate (5). The control contacts (4) are fixed on the lower surface of the unbendable projection (6). The plate (5) together with operating elements fixed thereto is enveloped with the waterproof film (10). The shape of the film (10) matches the external outlines of the plate (5) with edge allowance and the edge (11) thereof is provided with V-shaped notches (12). The device is made in standard (uniform) configuration of average anthropometric size from 25×25×2 mm to 40×40×5 mm with the possibility of its location inside the oral cavity.

The proposed device operates in the following manner.

Figure 3:
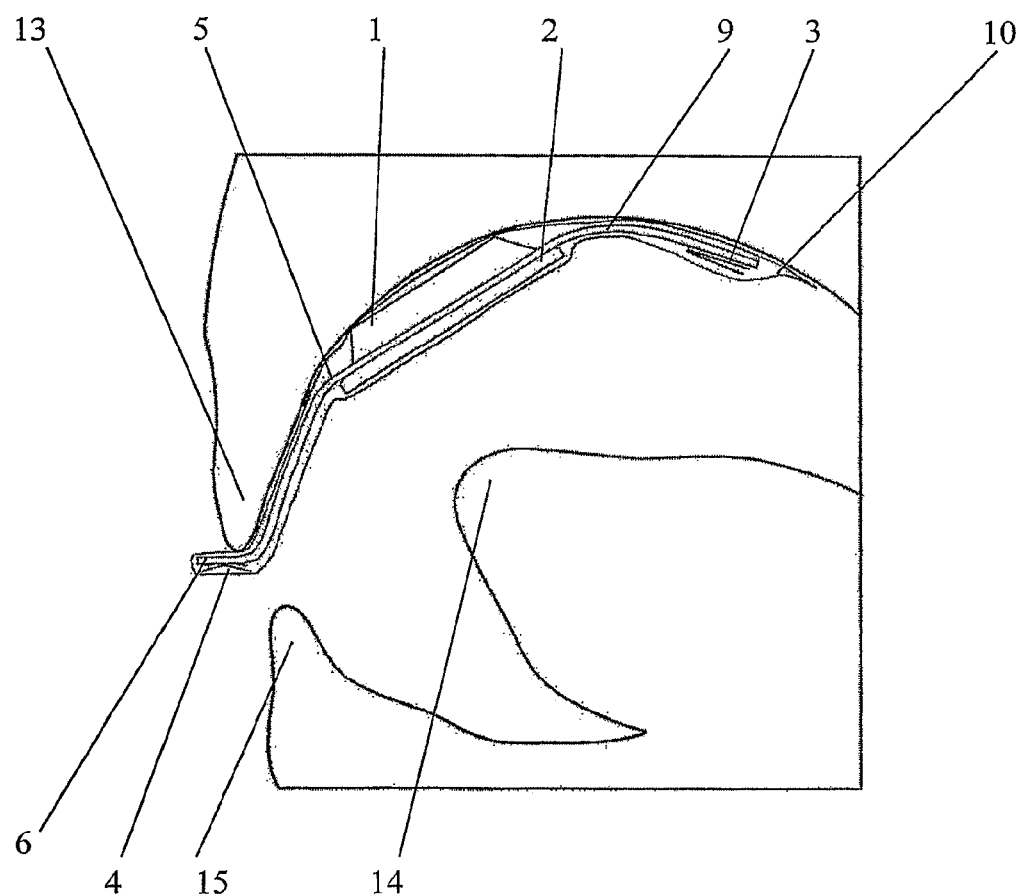
FIG. 3 shows the location of the device inside the human oral cavity.

The device is located in the oral cavity (FIG. 3) so that the front teeth (13) of the upper jaw are located on the unbendable projection (6) of the plate (5). Then the device is pressed against the hard palate by the tongue, and a negative pressure is created in the oral cavity between the hard palate mucosa and the film (10) by closing the lips, which results in deformation of the straps (9) in accordance with the arch of the hard palate, at that the film (10) sticks to the mucosa, and the notches (12) bears against the mucosa repeating its relief and preventing aspiration of liquid and air in the space between the mucosa and the device, which, in its turn, fixes the device in the predetermined position. The unit (2) specifying the coordinates and the functional contacts (3) for the keyboard functions remote control are controlled by the tip (14) of the tongue. The front teeth (15) of the lower jaw press the control contacts (4) performing the mouse buttons functions buttons and operating the device in this manner. Upon completion of the work the notches (12) of the film (10) is detached from the mucosa by the tip (14) of the tongue, the air infiltrates into the space between the mucosa and the device, and the device is pulled out of the oral cavity. Then the device is placed into a vessel containing antiseptic fluid for the purpose of hygiene.

The proposed device can be demanded by physically limited persons, in particular, by the persons with paralysis of upper and lower limbs, or persons whose occupation limits the use of hands.

What we claim is:

1. A remote device for controlling a computer by physically limited person made to allow its location in an oral cavity and including a signal processing and a transmitting module, a coordinate unit electrically connected with the module and controlling the cursor, at least three functional contacts for computer keyboard functions remote control, and at least two control contacts electrically connected with the module and performing mouse buttons functions, the device comprising:

an elastic basic plate which is symmetrical with respect to a longitudinal axis and is provided with an unbendable projection on the front part thereof;

the plate includes a central circle, at least three peripheral circles radially spaced away from the central circle, at least three connecting straps mating with the central circle by one end thereof, whilst the other end is coupled with the respective peripheral circle;

the unbendable projection is made in a shape of equailateral trapezoid adjacent to the central circle by the larger base thereof and is upwardly bent at about 20 to 60° angle with respect to the plate plane;

wherein the signal processing and transmitting module is arranged on the top surface of the central circle of the plate;

the coordinate unit is arranged on the lower surface of the central circle of the plate;

each functional contact is fixed to the lower surface of the respective peripheral circle of the plate;

the control contacts are fixed on the lower surface of the unbendable projection;

the plate together with operating elements fixed thereto is enveloped with a waterproof film;

wherein the shape of the film matches the external outlines of the plate with edge allowance and the edge thereof is provided with a plurality of notches.

* * * * *